US 6,551,297 B2

(12) United States Patent
Tanaka et al.

(10) Patent No.: US 6,551,297 B2
(45) Date of Patent: Apr. 22, 2003

(54) ABSORBENT ARTICLE

(75) Inventors: Masahito Tanaka, Tochigi (JP);
Mayumi Kimura, Tochigi (JP);
Hironori Kawasaki, Tochigi (JP);
Mitsugu Hamajima, Tochigi (JP);
Minoru Nakanishi, Tochigi (JP); Jinko Noguchi, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/180,479

(22) PCT Filed: May 30, 1997

(86) PCT No.: PCT/JP97/01858

§ 371 (c)(1),
(2), (4) Date: Jan. 11, 1999

(87) PCT Pub. No.: WO97/46185

PCT Pub. Date: Dec. 11, 1997

(65) Prior Publication Data

US 2002/0128625 A1 Sep. 12, 2002

(30) Foreign Application Priority Data

Jun. 4, 1996 (JP) .............................................. 8-141875
Jul. 22, 1996 (JP) .............................................. 8-191715

(51) Int. Cl.$^7$ .......................... A61F 13/18; A61F 13/20
(52) U.S. Cl. ................ 604/385.24; 604/366; 604/368; 604/375; 604/378; 604/385.01; 604/387
(58) Field of Search ................................. 607/385, 401, 607/368, 366, 367, 385.24–385.3, 387, 378, 385.01, 385.201, 385.21, 385.03, 385.23, 375, FOR 103, FOR 104

(56) References Cited

U.S. PATENT DOCUMENTS 3,441,023 A * 4/1969 Rijssenbeek ................. 604/378
3,731,688 A * 5/1973 Litt et al. ............. 604/385.201

(List continued on next page.)

FOREIGN PATENT DOCUMENTS

| EP | 2-311333 | | 4/1989 |
| FR | 2-488107 | | 2/1982 |
| FR | 2505619 | | 11/1982 |
| GB | 2-078811 | | 1/1982 |
| GB | 2 101 408 | * | 1/1983 |
| GB | 2-242610 | | 10/1991 |
| JP | 5711231 | | 1/1982 |
| JP | 5735002 | | 2/1982 |
| JP | 5756502 | | 4/1982 |
| JP | 603491 | | 1/1985 |
| JP | 3-123553 | * | 5/1991 |
| JP | 4152946 | | 5/1992 |
| JP | 586321 | | 11/1993 |
| JP | 6121810 | | 5/1994 |
| WO | 9004375 | | 5/1990 |
| WO | 9014814 | | 12/1990 |
| WO | 9306804 | | 4/1993 |

OTHER PUBLICATIONS

Translation of JP 3–123553, Oct. 1995.*
Patent Abstracts of Japan, vol. 18, No. 410 (c–1232), Aug. 2, 1994, A JP 61 121810 (Kao Corp).

*Primary Examiner*—Karin Reichle
(74) *Attorney, Agent, or Firm*—Birch, Stewart, Kolasch & Birch, LLP

(57) ABSTRACT

An absorbent article includes a liquid-permeable top layer, a liquid-impermeable back layer, and a liquid-retentive absorbent member interposed between the top layer and the back layer. The absorbent member is arranged such that a pair of absorbent barrier cuffs having a prescribed width are formed at respective left and right opposing side portions of the top layer in the width-wise direction thereof, and liquid-shrinkable members, which can elastically shrink upon absorption of liquid, are disposed within the barrier cuffs and extend in the longitudinal direction of the barrier cuffs.

20 Claims, 9 Drawing Sheets

U.S. PATENT DOCUMENTS

| | | | | |
|---|---|---|---|---|
| 3,860,003 A | * | 1/1975 | Buell | 604/385.25 |
| 3,929,134 A | * | 12/1975 | Karami | 604/378 |
| 3,995,640 A | * | 12/1976 | Schaar | 604/385.21 |
| 4,029,101 A | | 6/1977 | Chesky et al. | |
| 4,041,950 A | * | 8/1977 | Jones, Sr. | 604/385.28 |
| 4,081,301 A | * | 3/1978 | Buell | |
| 4,326,528 A | * | 4/1982 | Ryan et al. | 604/385.26 |
| 4,576,590 A | * | 3/1986 | Jackson et al. | 604/385.201 |
| 4,582,550 A | * | 4/1986 | Sigl | 604/385.24 |
| 4,695,278 A | * | 9/1987 | Lawson | 604/385.28 |
| 4,731,071 A | * | 3/1988 | Pigneul | 604/385.23 |
| 4,938,753 A | * | 7/1990 | Van Gompel et al. | 604/385.29 |
| 4,994,052 A | | 2/1991 | Kimura | |
| 5,175,046 A | | 12/1992 | Nguyen | |
| 5,735,838 A | * | 4/1998 | Ronnberg et al. | 604/385.25 |
| 5,954,705 A | * | 9/1999 | Suwaki et al. | 604/387 |
| 6,293,935 B1 | * | 9/2001 | Kimura et al. | 604/385.05 |

* cited by examiner

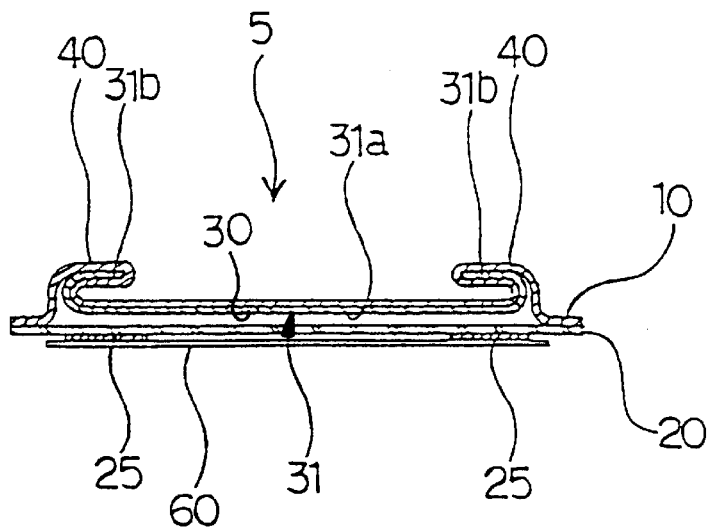
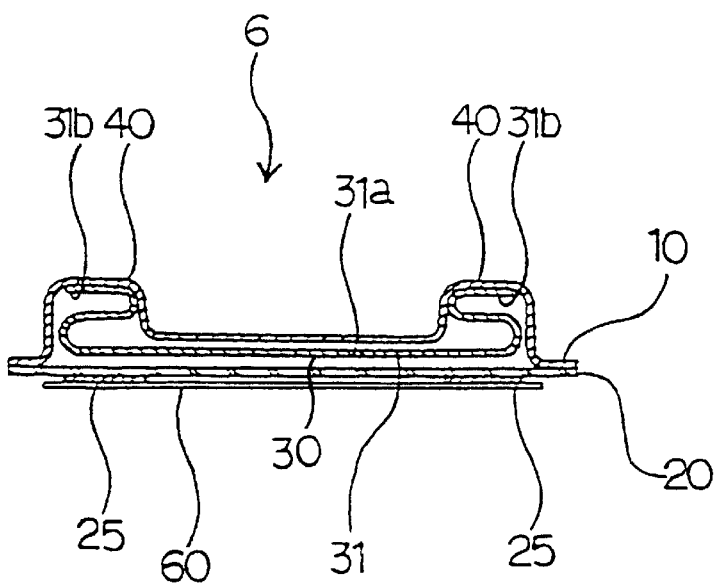
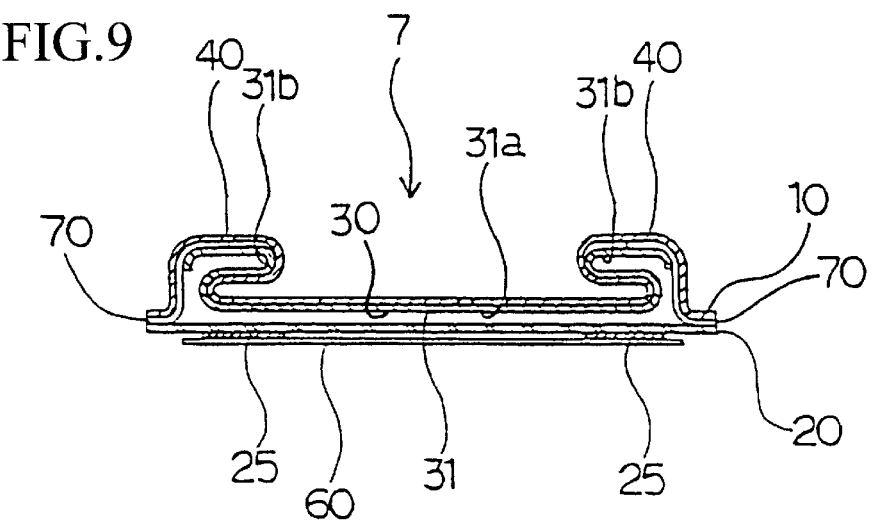

ABSORBENT ARTICLE

TECHNICAL FIELD

The present invention relates to an absorbent article, such as a sanitary napkin, an incontinent pad, a breastfeeding pad, and the like, including a liquid-permeable top layer, a liquid-impermeable back layer, and a liquid-retentive absorbent core disposed between the top layer and the back layer. More particularly, the present invention is directed to an absorbent article which is easy to manufacture, and capable of preventing liquid leakage, irrespective of the quantity of body fluid and motion of the wearer.

BACKGROUND ART

In general, absorbent articles such as a sanitary napkin, an incontinent pad, a breastfeeding pad, and the like are known to include a liquid-permeable top layer, a liquid-impermeable back layer, and a liquid-retentive absorbent core disposed between the top layer and the back layer. Such an absorbent article is required to cause body fluid, such as blood, urine, and the like, to rapidly migrate to the absorbent core where it is absorbed and retained with no leakage.

In order to absorb and retain body fluid with no leakage, heretofore, there has been utilized an absorbent article, as disclosed in Japanese Laid-Open Patent Publication No. 4(1992)-152946, Japanese Patent Publication No. 60(1985)-3491, and Japanese Laid-Open Utility Model Publication No. 5(1993)-86321, in which a leakage-preventive wall (or leakage-preventive barrier) is formed on each of the widthwise, left and right side portions, so as to prevent leakage of unabsorbed body fluid deposited on the surface of the top layer.

An absorbent article disclosed in Japanese Laid-Open Patent Publication No. 4(1992)-152946 includes a pair of left and right elastic members expanded in the vicinity of the opposite side portions of a longitudinal, generally central region, inside of a top material and in a longitudinal direction thereof. The individual ends of the elastic members are secured to the top material which is secured to the leakage-preventive material along the elastic members in the vicinity of the longitudinal opposite side portions of the elastic members.

An absorbent article disclosed in Japanese Patent Publication No. 60(1985)-3491 includes a pair of leakage-preventive walls (or barrier walls) formed by wrapping opposite sides of the leakage-preventive material from the back of the absorptive layer with opposite side edges thereof which project from the top surface of the absorptive layer. A liquid-permeable material and the leakage-preventive layer arranged on the top surface of the absorptive layer are fixed by press adhesion to opposite ends or area located at the outside of the opposite ends.

An absorbent article disclosed in Japanese Laid-Open Utility Model Publication No. 5(1993)-86321 includes a pair of leakage-preventive sheets, each disposed at opposite sides of a skin contacting surface along a longitudinal direction thereof. Each leakage-preventive sheet is provided on the distal end portion thereof with a thread rubber for erecting the leakage-preventive sheet. These leakage-preventive walls (or leakage-preventive barriers) are formed by using a top sheet which constitutes the top layer of the absorbent article and a back sheet which constitutes the back layer, or by alternatively using a nonwoven fabric and a film-like material.

However, since such a leakage-preventive wall of the absorbent article either has no liquid absorbing/retentive properties or has only small liquid absorbing/retentive properties, the body fluid tends to leak beyond the leakage-preventive walls when a large quantity of body fluid is deposited on the surface of the top layer, caused by motion of the user, or the like.

Further, as an absorbent article capable of absorbing/retaining a body fluid with no leakage, there has heretofore been known an absorbent article which employs a liquid-shrinkable member which tends to shrink elastically by absorbing a body fluid. Such an absorbent article has such an advantage that it can easily be manufactured in the state that the liquid-shrinkable member has no elasticity.

An absorbent article employing a liquid-shrinkable material is disclosed in Japanese Laid-Open Patent Publication No. 57(1982)-11231, in which a plurality of liquid-shrinkable members are disposed in parallel relation to each other in the longitudinal direction of the absorbent article, generally over an entire central portion at the inside of the absorbent member in a thickness-wise direction. Thus, when a body fluid invades, the absorbent member is subjected to a shirring treatment due to shrinkage of the liquid-shrinkable members. Another absorbent article is disclosed in Japanese Laid-Open Patent Publication No. 57(1982)-35002, in which liquid-shrinkable members are disposed outwardly at each side of the absorbent member in such a way as to cross the longitudinal direction of the absorbent article, so that when the body fluid invades, an external part of each opposing side of the absorbent member stands up due to the shrinkage of the liquid-shrinkable member. A third is disclosed in Japanese Laid-Open Patent Publication No. 6(1994)-121810, in which a three-dimensional gather formation body including liquid-shrinkable members disposed integrally with a gather-forming sheet in the longitudinal and widthwise directions thereof is disposed on a top material, so that when a body fluid invades, the three-dimensional gather formation body stands up from the top material due to shrinkage of the liquid-shrinkable member. In Japanese Laid-Open Publication No. 57(1982)-56502, a liquid-shrinkable member is disposed on an external part of each opposing side of an absorbent member along the absorbent article in a longitudinal direction thereof, so that when a body fluid invades, the absorbent article has a bent shape in the longitudinal direction due to shrinkage of the liquid-shrinkable member.

However, an absorbent article in which the absorbent member is subjected to shrinking treatment has shortcomings that since the liquid-shrinkable member is present generally over the entire central portion at the inside of the absorbing body in the thickness-wise direction thereof and the absorbent article, as a whole, is provided with small irregularities, leakage tends to occur due to the motion of the wearer. With respect to the absorbent article in which the external part of each opposing side of the absorbent member stands up and the absorbent article in which the three-dimensional gather formation body stands up, they have shortcomings in that since both the external part of each opposing side and the three-dimensional gather formation body which stand up, do not have a body fluid absorbing ability, leakage is likely to occur beyond the external part of each opposing side, due to the motion of the wearer. Also, with respect to the absorbent article which is bent in the longitudinal direction, since the liquid-shrinkable member is disposed at an external part of each opposing side of the absorbent body, the absorbent body does not shrink integrally with the liquid-shrinkable member, resulting in unfavorable possibilities wherein the absorbent article is not effectively bent, the fitness is degraded, and among all, the problem of a liquid leakage, which is most likely to occur, at the side edge of the absorbent article is not yet obviated. In addition, since no improvement is seen in the absorptive capacity of a body fluid in any of the above conventional absorbent articles, they cannot appropriately cope with a large quantity of body fluid, thus inevitably resulting in leakage.

It is, therefore, the object of the present invention, to provide an absorbent article which is easy to manufacture, which fits nicely to the wearer's body, irrespective of the quantity of bodily fluid and motion of the wearer, and which is capable of preventing the possible leakage of body fluid in a reliable manner.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DISCLOSURE OF THE INVENTION

The present invention has achieved the above object by providing an absorbent article comprising a liquid-permeable top layer, a liquid-impermeable back layer, and a liquid-retentive absorbent member, interposed between said top layer and said back layer, wherein said absorbent member is arranged such that a pair of absorbent barrier cuffs having a prescribed width are each formed at the left and right opposing side portions of said top layer in the widthwise direction thereof (this invention is hereinafter referred to as the "first aspect of the invention").

Also, the present invention has achieved the above object by providing an absorbent article comprising a liquid-permeable top layer, a liquid-impermeable back layer, and a liquid-retentive absorbent member, interposed between said top layer and said back layer, wherein said absorbent member is arranged such that a pair of absorbent barrier cuffs having a prescribed width are each formed at the left and right opposing side portions of said top layer in the widthwise direction thereof, and liquid-shrinkable members which can elastically shrink upon absorption of liquid are provided inside the edges of said barrier cuffs and located in the longitudinal direction of said barrier cuffs such that said barrier cuffs are shrunk in the longitudinal direction of said barrier cuffs over a prescribed length (this invention is hereinafter referred to as the "second aspect of the invention"). Liquid-shrinkable members referred to herein shrink upon absorption of liquid, such as water and body fluid.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 7 is a sectional view, corresponding to FIG. 2 of the first embodiment, showing an absorbent article according to still another embodiment of the present invention (the first aspect of the invention);

FIG. 8 is a sectional view, corresponding to FIG. 2 of the first embodiment, showing an absorbent article according to still another embodiment of the present invention (the first aspect of the invention);

FIG. 9 is a sectional view, corresponding to FIG. 2 of the first embodiment, showing an absorbent article according to the other embodiment of the present invention (the first aspect of the invention);

DETAILED DESCRIPTION OF THE INVENTION

Several embodiments of the absorbent article of the present invention will now be described with reference to the drawings. In any one of the first three embodiments, a liquid-permeable top sheet is used as a top layer and a liquid-impermeable back sheet is used as a back layer.

Figure 1:
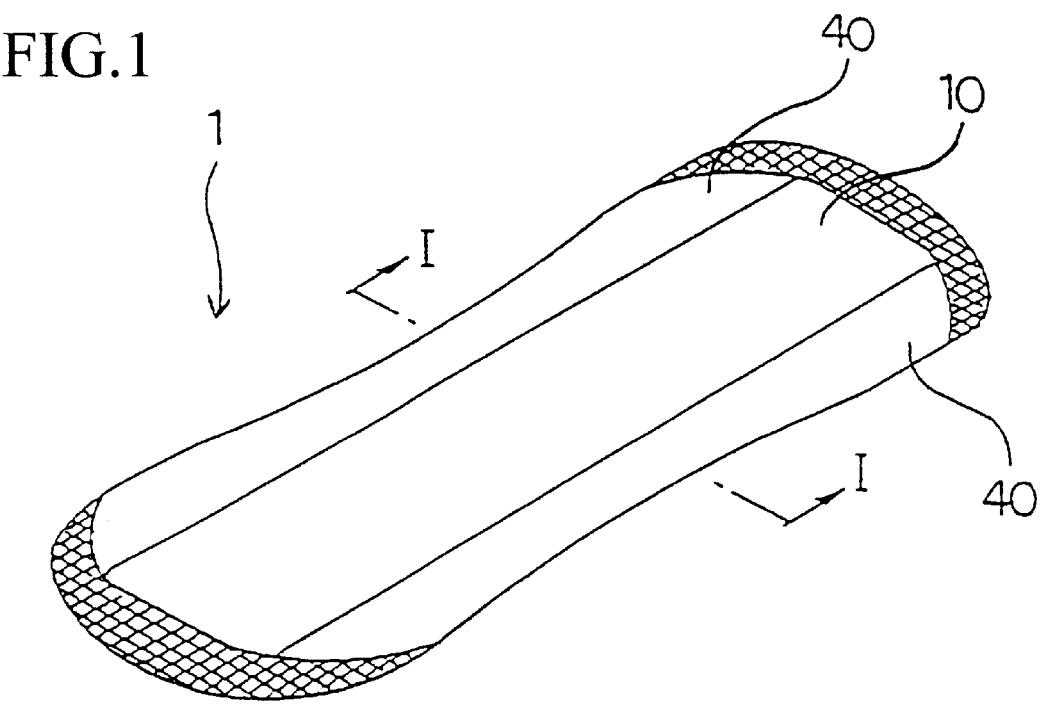
FIG. 1 is a perspective view showing an absorbent article according to the first embodiment of the present invention.
Figure 2:
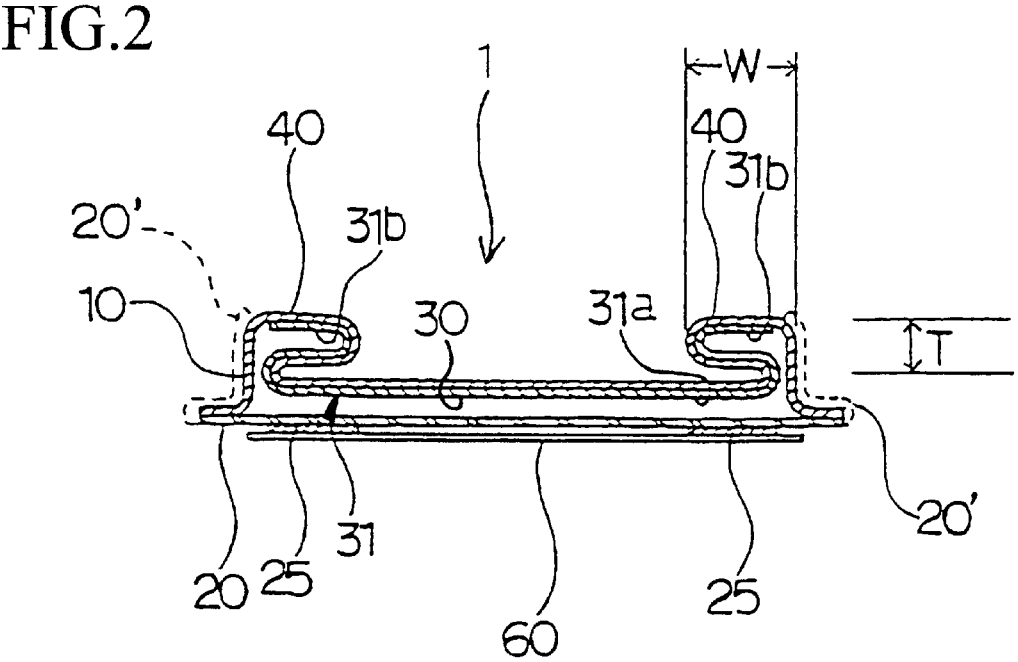
FIG. 2 is a sectional view taken along line I—I of FIG. 1.

FIG. 1 is a perspective-view showing a sanitary napkin as the first embodiment of the absorbent article of the present invention (the first aspect of the invention), and FIG. 2 is a sectional view, taken along line I—I of FIG. 1.

A sanitary napkin 1 according to this embodiment includes a liquid-permeable top layer 10, a liquid-impermeable back layer 20, and a liquid-retentive layer absorbent member 30 disposed between the top layer 10 and the back layer 20. This construction is the same as the prior art.

As shown in FIGS. 1 or 2, in the sanitary napkin 1 according to this embodiment, the absorbent member 30 is arranged such that a pair of absorbent barrier cuffs 40, 40 having a prescribed width are each formed from the absorbent member 30 and the top layer 10 at left and right opposing side portions of the top layer 10 in the widthwise direction thereof.

The absorbent member 30 consists only of an absorbent sheet 31 having a thickness of 0.3 mm to 5 mm. The absorbent sheet 31 comprises a basal bottom portion 31a, and a pair of side piece portions 31b, 31b each connected to the basal bottom portion 31a. The side piece portions 31b, 31b are folded inwardly to the side of said top layer 10 at left and right opposing side edges of the basal bottom portion 31a and then folded back outwardly to form an overlaid, serpentine, S-configuration at left and right opposing side portions of the basal bottom portion 31a. Folding portions of the absorbent sheet 31 are located along the longitudinal direction of the sanitary napkin 1, and the left and right opposing side portions of the absorbent sheet 31 are folded twice and overlaid to form the barrier cuffs 40, 40. The absorbent sheet 31 is preferably 0.3 mm to 5 mm in thickness, more preferably 0.3 mm to 3 mm, and more preferably 0.3 mm to 1.5 mm. If the thickness is less than 0.3 mm, it is difficult to provide the barrier cuffs 40, 40 capable of sufficiently exhibiting the effects of the present invention, i.e. that the fitness is improved, the capacity for absorbing a body fluid is increased, and so forth. In addition, the sheet 31 tends to be twisted when folded. In contrast, if the thickness is more than 5 mm, the rigidity of the absorbent sheet 31 is overly increased to spoil the fitness. Thus, the desired effect cannot be obtained and the perception of disorder is given to the wearer.

The absorbent sheet 31 is overlaid in superimposed relation with the top layer 10 over its entire surface. The absorbent sheet 31 and the top layer 10 folded integrally with the absorbent sheet 31 are overlaid in a belt-like configuration at the lateral left and right opposing side portions of the sanitary napkin 1. The overlaid structure of the absorbent sheet 31 and top layer 10 may be achieved by attachment using an adhesive agent or heat sealing, aside from a simple placement on the top layer 10 upon the absorbent sheet 1. The top layer 10 is extended to a perimeter of the absorbent sheet 31 and secured to the back layer 20 at the perimeter of the absorbent sheet 31.

The back layer 20 is applied at its outer surface with a viscous agent to thereby form two viscous portions 25, 25 in the longitudinal direction of the back layer 20. The viscous portions 25, 25 are each covered with a peelable paper 60. This peelable paper 60 is peeled off immediately before the sanitary napkin 1 is utilized, so that the viscous portions 25, 25 are exposed. The viscous portions 25, 25, when worn, are adhered to the clothing in order to prevent slippage of the sanitary napkin 1.

The absorbent sheet 31 can be absorbent paper, nonwoven fabric, a pulp sheet made of fibers and a binder, fluff pulp, a sheet obtained by interposing a superabsorbent polymer between paper or nonwoven fabrics or between paper and nonwoven fabric in an overlaid configuration or a sheet made of a mixture of a superabsorbent polymer and fiber or hydrophilic fiber, and the like. A sheet of a mixture of a superabsorbent polymer or hydrophilic fiber is preferred for its absorptivity for a body fluid (a sheet obtained by admixing a hydrophilic fiber, a superabsorbent polymer and a binder, and forming it into a sheet-like shape). The superabsorbent polymer in the sheet may be dispersed either in layers or in three dimensions.

The above-described fiber or hydrophilic fiber preferably includes cellulose fiber, such as wood pulp; regenerated cellulose fiber, such as viscous rayon and cuprammonium rayon; synthetic hydrophilic fiber, such as polyvinyl alcohol fiber and polyacrylonitrile fiber; and synthetic fiber with the surface thereof rendered hydrophilic with a surface active agent, etc., such as polyethylene fiber, polypropylene fiber, polyethylene terephthalate fiber, polyethylene/polypropylene conjugate fiber, and polyethylene/polyethylene terephthalate conjugate fiber. Cellulose fibers are preferred for their satisfactory retention of hydrophilic properties.

The superabsorbent polymer which can be used in the absorbent sheet 31 is preferably the one capable of absorbing and retaining 20 or more times as much liquid as its own weight and gelling upon liquid absorption. Such superabsorbent polymers include starch, crosslinked carboxymethylated cellulose, polyacrylic acid or a salt thereof, and a polyacrylate graft polymer. The polyacrylate is preferably sodium polyacrylate. Acrylic acid copolymers containing a comonomer, such as maleic acid, itaconic acid, acrylamide, 2-acrylamide-2-methylpropanesulfonic acid, 2-(meth)acryloylethanesulfonic acid, 2-hydroxyethyl (meth)acrylate or styrenesulfonic acid, in such a proportion that does not impair its performance as a superabsorbent polymer, can also be preferably used.

Particularly preferred are superabsorbent polymers capable of absorbing and retaining a large quantity of liquid through ionic osmosis and yet having no leaks even under pressure, comprising water-insoluble and hydrophilic crosslinked polymer particles which are obtained by polymerizing acrylic acid or an alkali salt thereof (e.g. sodium or potassium), etc. followed by crosslinking for water insolubilization.

The binder which can be used in the formation of the absorbent sheet 31 preferably includes thermally fusible bonding fiber and/or a strengthening assistant from the standpoint of wet strength of the resulting sheet.

The thermally fusible bonding fiber can be fibers which are fused upon heating and adhere to each other. Such thermally fusible bonding fibers include polyolefin fiber, such as polyethylene, polypropylene, and polyvinyl alcohol; polyester fiber, polyethylene/polypropylene conjugate fiber, polyethylene/polyester conjugate fiber, low-melting polyester/polyester conjugate fiber, polyvinyl alcohol/polypropylene conjugate fiber having a hydrophilic surface, and polyvinyl alcohol/polyester conjugate fiber. The conjugate fibers may be either a core sheath-type or a side-by-side type. These thermally fusible bonding fibers can be used either individually or as a mixture of two or more thereof. The thermally fusible bonding fiber which can be preferably used in the present invention, which is one aspect of the present invention, includes polyvinyl alcohol fiber soluble in hot water and a core sheath-type polyester fiber. In general, these thermally fusible bonding fibers preferably have a fiber length of 2 to 60 mm and a fiber diameter of 0.1 to 3 deniers, particularly 0.5 to 3 deniers.

The strengthening assistant includes a polyamine epichlorohydrin resin, dialdehyde starch, sponge, and carboxymethyl cellulose.

A preferred absorbent sheet 31 is the one made up of a hydrophilic fiber, a thermally fusible bonding fiber or a strengthening assistant, and a superabsorbent polymer. The superabsorbent polymer is not present on the absorbent surface of the absorbent sheet for absorbing liquid but distributed inside the absorbent sheet, and adheres to the hydrophilic fiber constituting the absorbent sheet. The superabsorbent polymer is spread in an amount of 5 to 300 g/m² of the absorbent sheet and the absorbent sheet has a thickness of 0.3 to 1.5 mm.

A still more preferred absorbing sheet 31 is composed of a fibrous structure made up of bulky hydrophilic fiber and thermally fusible bonding fiber or a strengthening assistant and superabsorbent polymer particles and having a thickness of 0.3 to 1.55 mm, in which the superabsorbent polymer particles do not exist on the absorbing surface of the absorbent sheet but is dispersed and fixed in the inside of the fibrous structure, and the superabsorbent polymer is used in a basis weight of 20 to 70 g/m².

In such an absorbent sheet, since a superabsorbent polymer is fixedly dispersed in a single sheet in a three-dimensional pattern, the absorption ability of the superabsorbent polymer is effectively exhibited. Moreover, the gel blocking of the polymer is less. Accordingly, a body fluid tends to pass through the absorbent sheet smoothly. Thus, the absorbent sheet can advantageously be used in order to obtain a high absorption ability.

In order for the barrier cuffs 40, 40 not to give the perception of disorder to the wearer and in order for the absorbent sheet to exhibit a favorable absorptive capacity of bodily fluids at the barrier cuffs 40, 40, the barrier cuffs are preferably 1 to 10 mm in height T, 5 mm to 30 mm in width W and preferably 5% to 40% of the smallest width (width between I—I of FIG. 1) of the sanitary napkin 1. If the height is less than 1 mm, there is the possibility that the leakage of body fluid cannot be effectively avoided. In contrast, if the height is more than 10 mm, the perception of disorder is given to the wearer.

As the viscous agent for forming the viscous portions 25, 25 and as the peelable paper 60, any one selected from those which have heretofore been used can be selected with no special limitation.

According to the sanitary napkin of this embodiment, the pair of barrier cuffs 40, 40 function as a leakage-preventive wall (or barrier) and prevent body fluid still remaining on the top layer 10 without being absorbed, from flowing out of the left and right opposing side portions of the napkin.

Further, in the sanitary napkin of this embodiment, since the pair of barrier cuffs 40, 40 each include an absorbent sheet 31 and have a high absorptive capacity for body fluid, a large quantity of body fluid can also be absorbed at the left and right opposing side portions. Therefore, according to the sanitary napkin 1 of this embodiment, a possible leakage of body fluid from the left and right opposing side portions can be prevented in an efficient manner.

According to the sanitary napkin of this embodiment, since the absorbent member 30 on the side of top layer 10 is the absorbent sheet 31 of 0.3 mm to 5 mm in thickness, twisting seldom occurs, the perception of disorder is not given to the wearer, and a sufficient absorptive capacity of body fluid is exhibited.

According to the sanitary napkin of this embodiment, the barrier cuffs 40, 40 are formed by folding the absorbent sheet having a thickness of 0.3 mm to 5 mm and having a height equal to at least about 1 mm when in combination with the top layer 10. Therefore, the possible leakage from the opposing side portions can effectively be prevented.

According to the sanitary napkin of this embodiment, since the top layer 10 is folded and overlaid together with the absorbent sheet 31, a body fluid finds it difficult to migrate to the left and right opposing side portions and the top layer 10 as well and thus the possible leakage of body fluid can be prevented in a more efficient manner.

Figure 3:
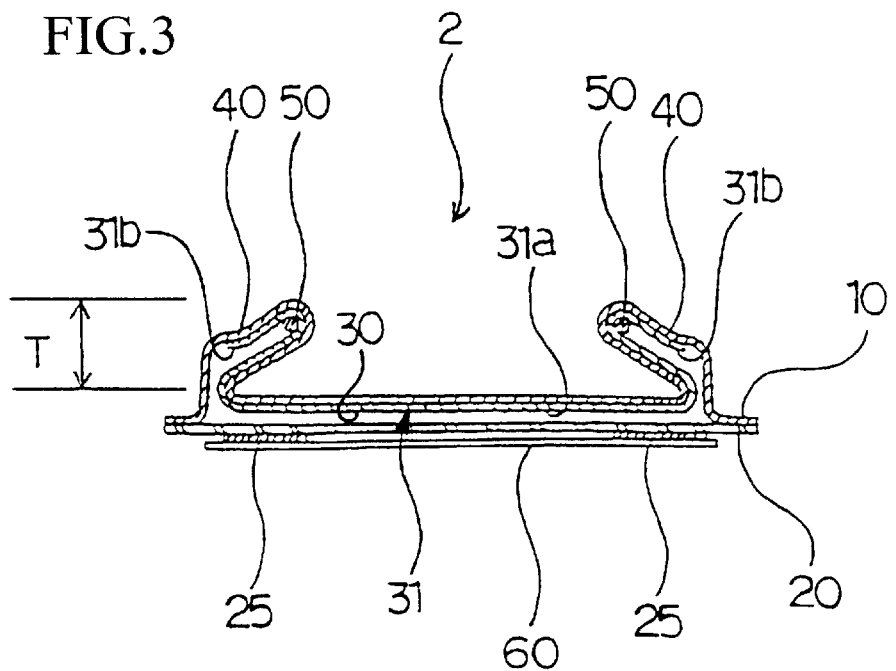
FIG. 3 is a sectional view, corresponding to FIG. 2 of the first embodiment, showing an absorbent article according to a second embodiment of the present invention (the first aspect of the invention)
Figure 4:
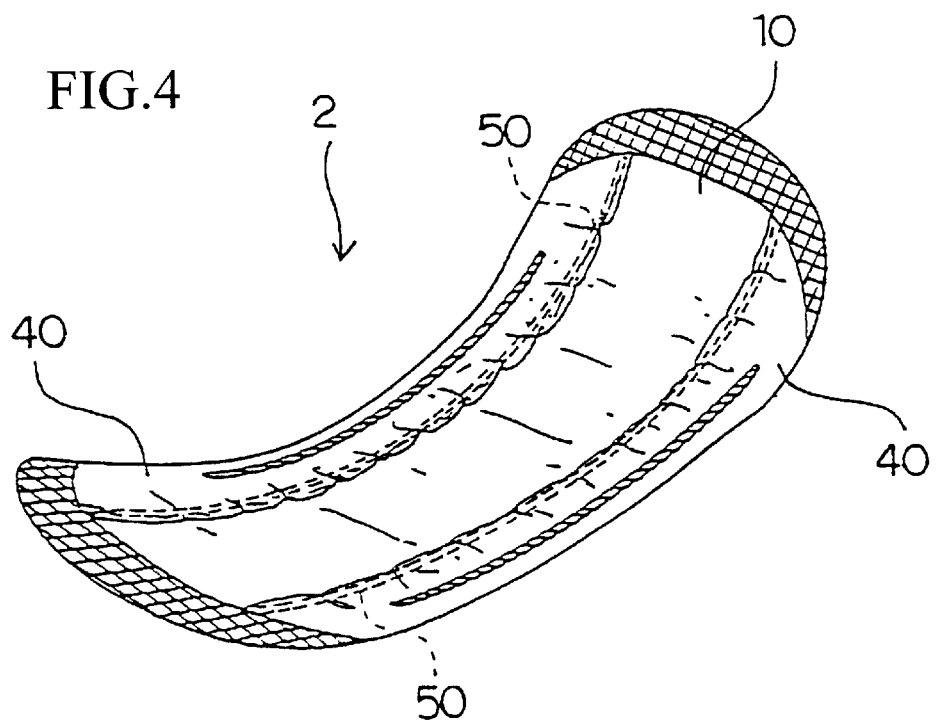
FIG. 4 is a perspective view showing the absorbent article of FIG. 3.

FIG. 3 is a sectional view similar to FIG. 2 of the first embodiment, showing a second embodiment of an absorbent article according to the present invention (the first aspect of the invention), and FIG. 4 is a perspective view showing the sanitary napkin of FIG. 3. In this embodiment, those members identical with the first embodiment of FIGS. 1 and 2 are denoted by identical reference numerals, with the description thereof being omitted.

As shown in FIGS. 3 and 4, in the sanitary napkin 2 of this embodiment, a pair of elastic members 50, 50 are provided along the inside, side edges of the barrier cuffs 40, 40 located in the longitudinal direction of the barrier cuffs 40, 40 such that the barrier cuffs 40, 40 are shrunk in the longitudinal direction thereof over a prescribed length.

This embodiment is now described in more detail. In this embodiment, the elastic members 50, 50 are, in their expanded status, fixedly secured at the folded portions of the side piece portions 31b, 31b approximately over the entire length from the side of the back layer 20, such that gathers are formed when the folded portions are shrunk.

As the elastic members 50, 50, a film, a fiber, a foamed body and the like composed of a polymer of a number of rubbers, such as polyurethanes, polybutadiene, isoprene and the like, ethylene-vinyl acetate, and a number of polyolefins having extensibility can be used. In order to exhibit a favorable effect without degrading the comfortable wearing perception, the elastic members 50, 50 are preferably 10 gf to 300 gf in stress at 30% expansion.

The elastic members 50, 50 are not particularly limited in position and length for arrangement. However, in order to bend the barrier cuffs 40, 40 such that they favorably comply with the wearer, the elastic members 50, 50 are preferably arranged over a length 15% to 90% of the entire longitudinal length of the sanitary napkin 2. In accordance with the contraction of the elastic members 50, 50 in the longitudinal direction, the barrier cuffs 40, 40 stand in the upper direction thereby preventing liquid leakage more securely. The height T of the barrier cuffs 40, 40 becomes higher than that in the case where no elastic members are provided, and is preferably 1 to 30 mm, more preferably 3 to 30 mm.

All the construction other than the arrangement of the elastic members 50, 50 of this embodiment is the same as the aforementioned first embodiment. The absorbent sheet 31 is preferably composed of other material than fluff pulp. The reason is that an absorbent sheet using fluff pulp occasionally ruptures with shrinkage of the elastic members 50, 50.

The sanitary napkin 2 of this embodiment can also provide the same function and effect as in the first embodiment.

According to the sanitary napkin 2 of this embodiment, since the barrier cuffs 40, 40 each include an absorbent sheet 31 having a thickness of 0.3 mm to 5 mm, the elastic members 50, 50 can easily be secured to the inside of the barrier cuffs 40, 40.

According to the sanitary napkin 2 of this embodiment, the absorbent sheet 31 is shrunk by the elastic members 50, 50 over a prescribed length in the longitudinal direction and bent, as shown in FIG. 4, in the longitudinal direction in such a way as to comply with the wearer's contacted part, and the barrier cuffs 40, 40 are held in their upstanding postures on the wearer's skin side. Accordingly, the possible leakage of body fluid can more effectively be prevented.

According to the sanitary napkin 2 of this embodiment, since the elastic members 50, 50 are secured to the thin absorbent sheet 31, the frill-like irregularities formed at the barrier cuffs 40, 40 by shrinkage of the elastic members 50,

50 are comparatively small. Also, the good touch to the wearer's skin is hardly degraded on the side of the top layer 10, and a comfortable wearing perception is maintained.

Figure 5:
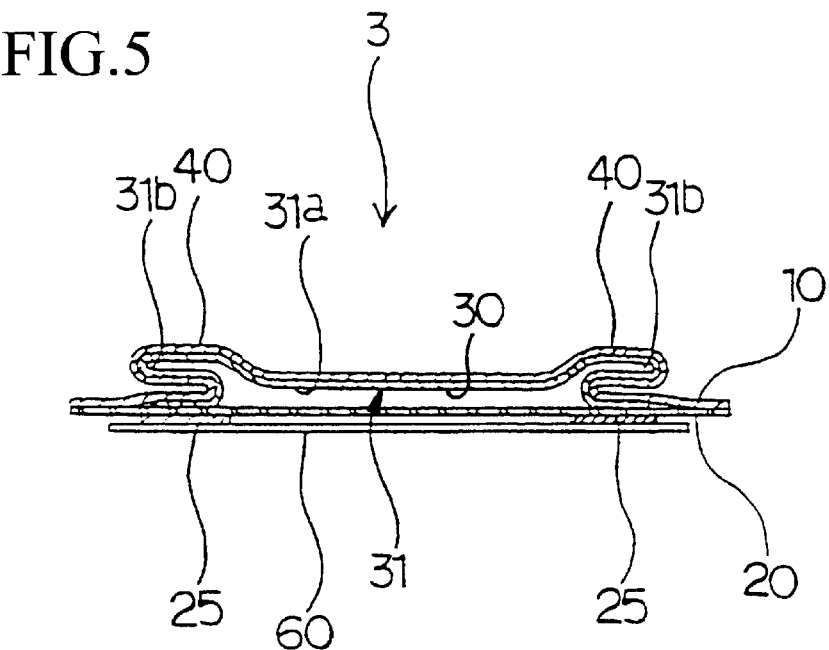
FIG. 5 is a sectional view, corresponding to FIG. 2 of the first embodiment, showing an absorbent article according to a third embodiment of the present invention (the first aspect of the invention)

FIG. 5 is a sectional view, corresponding to FIG. 2 of the first embodiment, showing a sanitary napkin as the third embodiment of an absorbent article of the present invention (the first aspect of the invention). In this embodiment, those members identical with the first embodiment of FIGS. 1 and 2 are denoted by identical reference numerals, and description thereof is omitted.

As shown in FIG. 5, in a sanitary napkin 3 of this embodiment, the side piece portions 31b, 31b of the absorbent sheet 31 are folded inwardly to the side of the back layer 20 at the left and right opposing side edges of the basal bottom portion 31a and then folded back outwardly to form an overlaid configuration at the left and right opposing side portions of the basal bottom portion 31a. The top layer 10 is folded integrally with the absorbent sheet 31 in the same manner as the absorbent sheet 31.

All the construction other than the folded form of the absorbent sheet 31 and the top layer 10 of this embodiment is the same as the aforementioned first embodiment.

According to the sanitary napkin 3 of this embodiment, due to the provision of providing a pair of barrier cuffs 40, 40, the body fluid still deposited on the top layer 10 without being absorbed is prevented from flowing to the left and right opposing side portions. However, a large quantity of body fluid is absorbed and the possible leakage of body fluid can effectively be prevented at the left and right opposing side portions.

The present invention (the first aspect of the invention) should not be limited to the above-mentioned first through third embodiments. The specific shape, dimension, etc. of each member can be appropriately modified without departing from the spirit and scope of the present invention.

Figure 6:
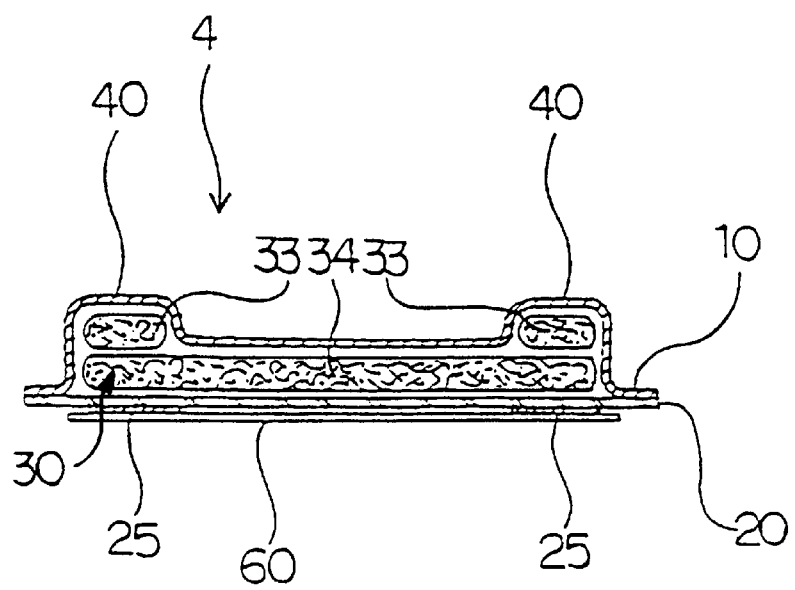
FIG. 6 is a sectional view, corresponding to FIG. 2 of the first embodiment, showing an absorbent article according to another embodiment of the present invention (the first aspect of the invention)

For example, in the first three embodiments, the absorbent member 30 may be formed as an absorbent pad. As to such a sanitary napkin, FIG. 6 shows a sanitary napkin 4 in which the absorbent member 30 of the first embodiment shown in FIGS. 1 and 2 is composed of absorbent pads 33, 33, 34.

Further, in the first three embodiments, an auxiliary sheet composed of a sheet similar to the absorbent sheet 31, and an absorbent pad such as pulp, may be arranged on the back layer 20, on the side of top layer 10, and on the side of the basal bottom portion 31a of the absorbent sheet 31, together with the absorbent sheet 31, so that the absorptive capacity of body fluid is increased. This auxiliary sheet may extend outwardly beyond the side edge of the absorbent sheet 31.

Furthermore, as shown in FIG. 7, the sanitary napkin may be designed such that the absorbent sheet 31 has side piece portions 31b, 31b superposed upon the left and right opposing side portions of the side of the top layer 10 inwardly from the left and right opposing side edges of the basal bottom portion 31a without being folded back, with the free end portions of the side piece portions 31b, 31b being arranged inside of the left and right opposing side edges of the basal bottom portion 31a.

In the first three embodiments, by folding the absorbent sheet 31 into an overlaid configuration from the vicinity of each side edge of the back layer 20, the absorbent sheet can obtain the same effect as the auxiliary sheet.

In the first three embodiments, the side piece portions 31b, 31b of the absorbent sheet 31 may be folded and superposed one upon another so that a greater number of layers are formed.

In the first three embodiments, the multilayered structure in the barrier cuffs 40, 40 may be formed by a plurality of absorbent sheets. In this case, the absorbent sheets may simply be arranged in superimposed relationship, or may be joined under pressure at their entire opposing surfaces, or may be partially joined at their opposing surfaces by an adhesive agent, or the like.

In the first three embodiments, it is also acceptable that the entire surface of the absorbent sheet 31 is not overlaid with the top layer 10 and only the surface of the folded absorbent sheet 31, which surface is exposed without being folded, may be overlaid with the top layer 10. Such a sanitary napkin, can be seen in FIG. 8, which shows a sanitary napkin 6 in which only a portion of the surface of the absorbent sheet 31, which surface is exposed without being folded, is overlaid to the top layer 10.

In the first three embodiments, it is also acceptable that the side edge portions of the back layer 20 are extended to form leakage-preventive barriers 20', 20' at the side outwardly of the absorbent member 30 as indicated by dotted lines of FIG. 2 or leakage-preventive materials 70, 70, having liquid-impermeable properties, are arranged as shown in FIG. 9, so that the possible leakage of body fluid is more reliably prevented. The leakage-preventive barriers 20', 20' or the leakage-preventive materials 70, 70 may be disposed between the absorbent member 30 and the top layer 10, or they may be arranged outwardly of the top layer 10. In case the leakage-preventive barriers 20', 20' and the leakage-preventive materials 70, 70 are utilized, they are slightly stood up by firmly attaching the top layer 10 and the leakage-preventive barriers 20', 20' or leakage-preventive materials 70, 70 to the back layer 20 at the perimeter of the absorbent sheet 31 by heat fusion bonding. Due to this arrangement, a more favorable effect can be obtained.

In the first three embodiments, as shown in FIG. 9, the side piece portions 31b, 31b of the absorbent sheet 31 may be extended outwardly from the left and right opposing side edges of the basal bottom portion 31a.

In the first embodiment of FIGS. 1 and 2, the absorbent sheet 31 and the top layer 10 may be formed into a single sheet.

The folding form of the absorbent sheet, the covering form of the absorbent sheet with the top layer, with or without the elastic members, and so forth are mutually replaceable in the first three embodiments. For example, in the first embodiment of FIGS. 1 and 2 and in the third embodiment of FIG. 5, there may also be a provision for the elastic members as in the second embodiment of FIGS. 3 and 4.

In the first three embodiments, the absorbent article may be something other than the sanitary napkin, such as an incontinent pad, breastfeeding pad, and the like.

Several embodiments of an absorbent article according to the present invention (the second aspect of the invention) will now be described specifically with reference to the drawings. In the first and second embodiments, a liquid-permeable top sheet is used as a top layer, and a liquid-impermeable back sheet is used as the back layer.

Figure 10:
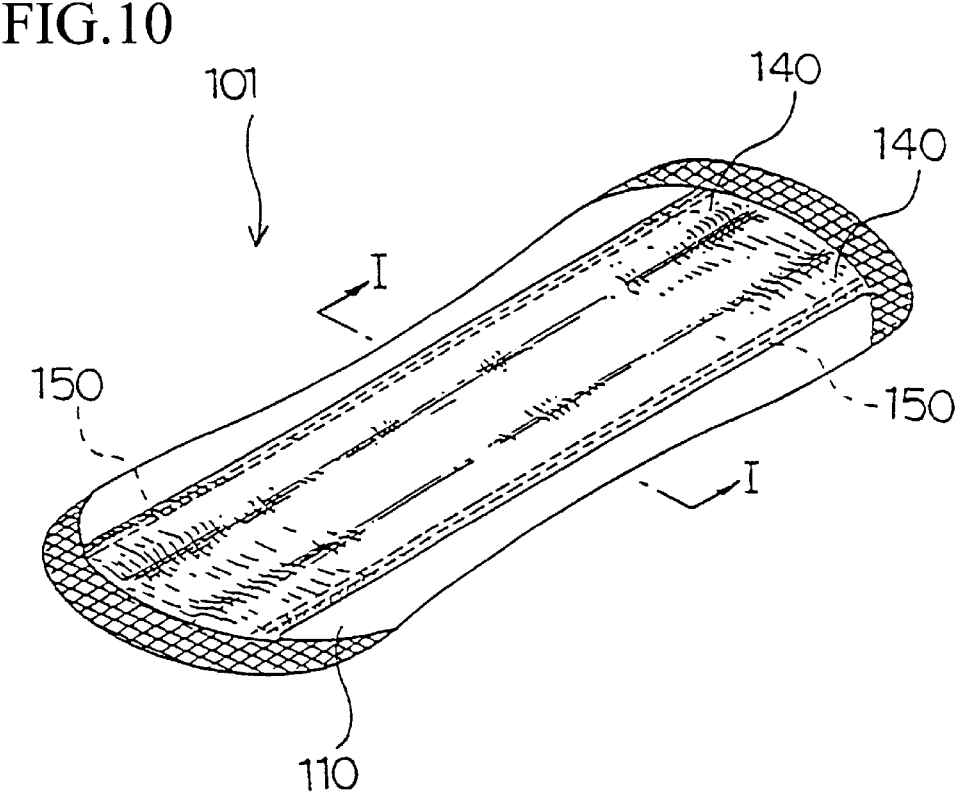
FIG. 10 is a perspective view showing a sanitary napkin as the first embodiment of an absorbent article of the present invention (the second aspect of the invention)
Figure 11:
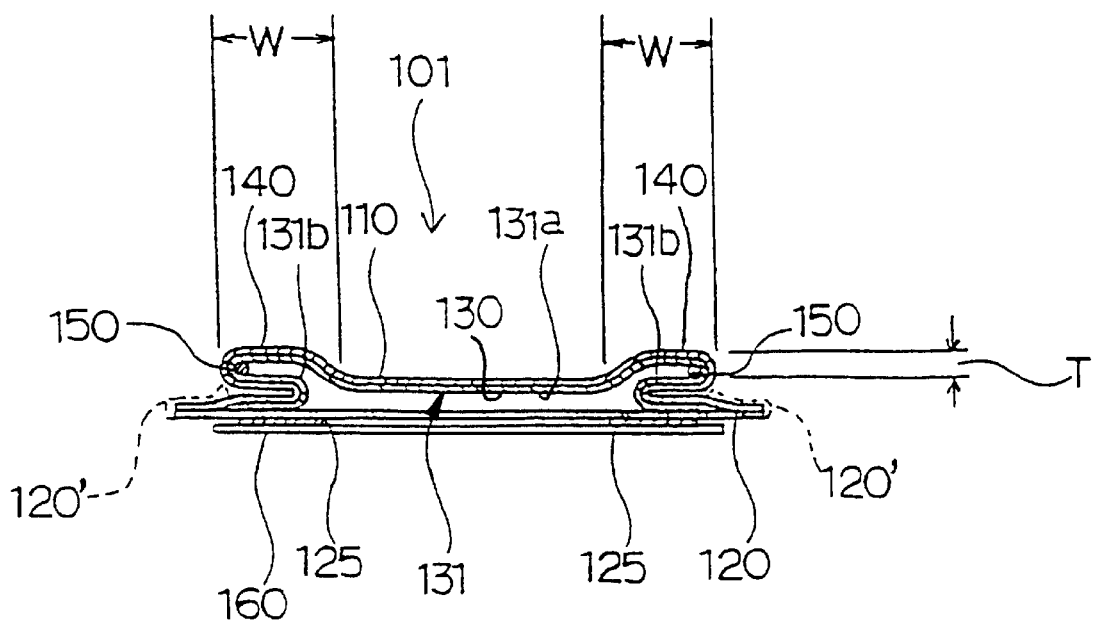
FIG. 11 is a sectional view, taken along line I—I, of FIG. 10, when viewed in the direction as indicated by arrows.
Figure 12:
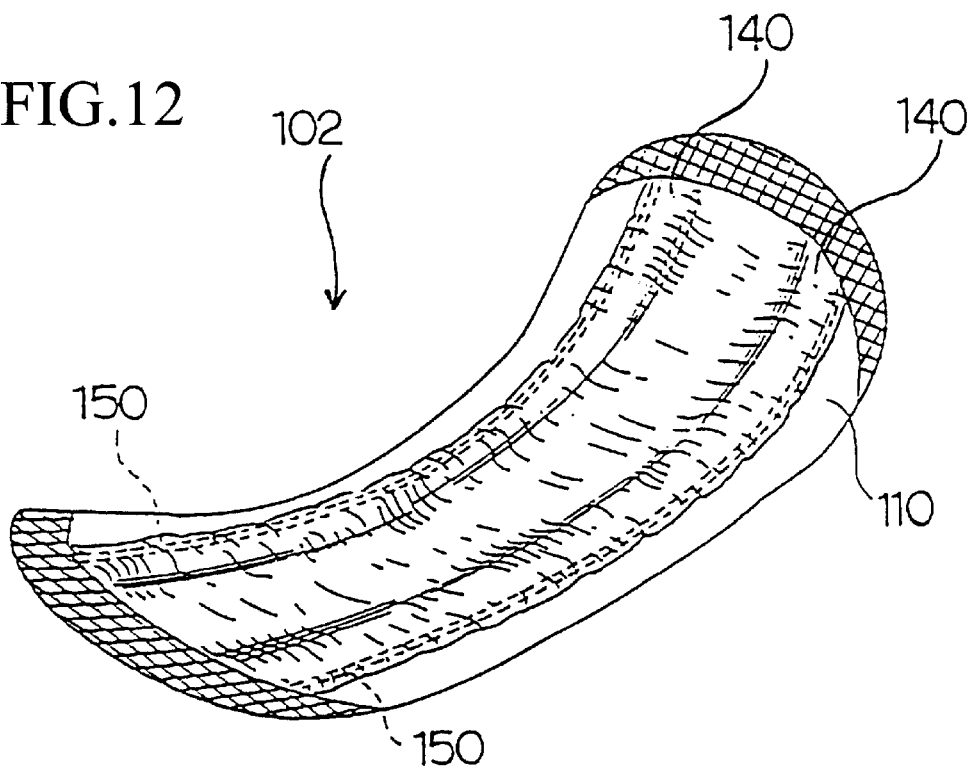
FIG. 12 is a perspective view showing a state of the sanitary napkin of FIG. 10 after absorption of a body fluid.
Figure 13:
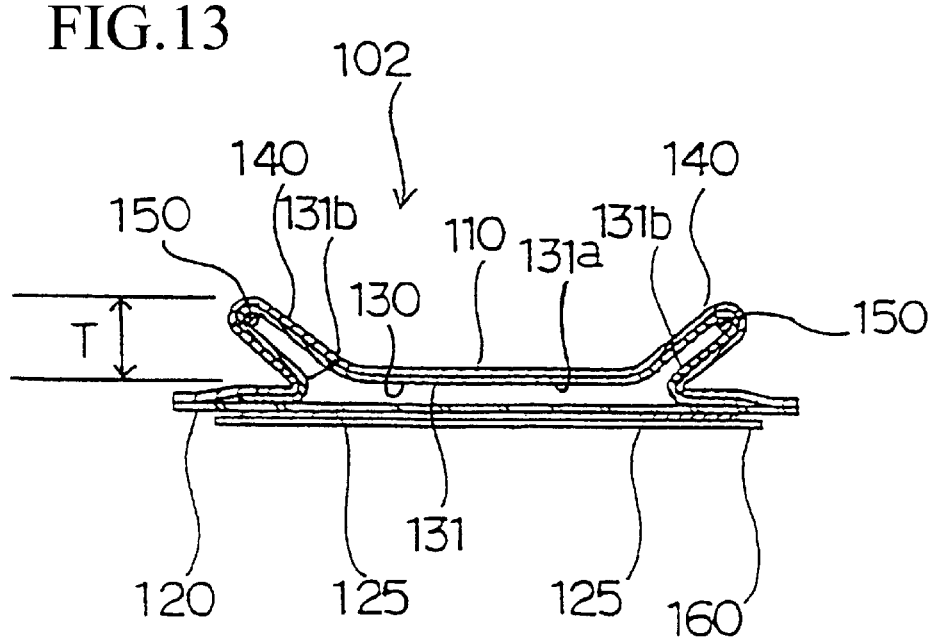
FIG. 13 is a sectional view, taken on line I—I, showing the state of the sanitary napkin of FIG. 10 after absorption of a body fluid, when viewed in a direction as indicated by the arrows.

FIG. 10 is a perspective view showing a sanitary napkin as the first embodiment of an absorbent article according to the present invention (the second aspect of the invention) and FIG. 11 is a sectional view taken along line I—I of FIG. 10 when viewed in the direction as indicated by the arrows. FIG. 12 is a perspective view showing the state of the sanitary napkin of FIG. 10 after absorption of a body fluid, and FIG. 13 is a sectional view taken along line I—I of the sanitary napkin of FIG. 10 after absorption of a body fluid when viewed in the direction as indicated by the arrows.

As shown in FIGS. 10 or 11, a sanitary napkin 101 includes a liquid-permeable top layer 110, a liquid-impermeable back layer 120, and a liquid-retentive absorbent member 130 disposed between the top layer 110 and the back layer 120. This construction is the same as the prior art.

In the sanitary napkin 101 of this embodiment, the absorbent member 130 is arranged such that a pair of absorbent barrier cuffs 140, 140 each having a prescribed width are formed on opposing side. Portions of the top layer 110. Liquid-shrinkable members 150, 150, each capable of elastically shrinking by absorbing a liquid are disposed inside the side edges of the pair of barrier cuffs 140, 140 located along the longitudinal direction thereof such that the pair of barrier cuffs are elastically shrunk along the longitudinal direction thereof over a prescribed length.

This embodiment is described in details. The absorbent member 130 is composed only of the absorbent sheet 131 having a thickness of 0.3 mm to 5 mm. The absorbent sheet 131 is folded into an overlaid configuration with its folding portion located in a longitudinal direction of the sanitary napkin 101, to thereby form a pair of the barrier cuffs 140, 140. The liquid-shrinkable members 150, 150 are secured to the absorbent sheet 131.

This embodiment is described in more detail. The absorbent sheet 131 includes a central band-like portion 131a, and a pair of side piece portions 131b, 131b connected to the central band-like portions 131a. The side piece portions 131b, 131b are folded inwardly to the side of the back layer 120 at the left and right opposing side edges of the central band-like portion 131a and superimposed upon the left and right opposing side portions of the central band-like portion 131a, and thereafter, are folded back outwardly in the widthwise direction. The liquid-shrinkable members 150, 150 are secured to the connecting portions between the central band-like portion 131a and the side piece portions 131b, 131b at the point where the central band-like portion 131a contacts the side piece portions 131b, 131b. The liquid-shrinkable members 150, 150 are disposed at the connecting portions over the entire length thereof, so that upon absorbing a body fluid, the barrier cuffs 140, 140 are elastically shrunk over their entire length in the longitudinal direction to thereby form gathers.

The absorbent sheet 131 is overlaid at its entire surface with the top layer 110, and the top layer 110 is folded integrally with and in the same folding configuration as the absorbent sheet 131. The overlaid structure of the absorbent sheet 131 and top layer 110 may be achieved by attaching them together using an adhesive agent or heat sealing, aside from a simple placement of the top layer 110 upon the absorbent sheet 131. The top layer 110 is extended to a perimeter of the absorbent sheet 131 and secured to the back layer 120 at the perimeter of the absorbent sheet 131.

The back layer 120 is applied at its outer surface with a viscous agent to thereby form two elongated viscous portions 125, 125 extending in the longitudinal direction of the back layer 120. The viscous portions 125, 125 are each covered with a peelable paper 160. This peelable paper 160 is peeled off immediately before the sanitary napkin is worn, so that the viscous portions 125, 125 are exposed. During usage, the viscous portions 125, 125 adhere to the clothing in order to prevent slippage of the sanitary napkin 101.

With respect to the absorbent sheet 131, one which is generally the same as the first embodiment of the invention can be used. The absorbent sheet 131 is preferably composed of material other than fluff pulp. The reason is that an absorbent sheet using a fluff pulp occasionally ruptures in accordance with shrinkage of the liquid-shrinkable members 150, 150.

The absorbent sheet 131 is preferably one having a superabsorbent ability so that its liquid-shrinkable member is not overly shrunk. Preferably, the absorbent sheet is what is obtained by mixing a superabsorbent polymer with a fiber and forming the mixture into a sheet-like shape as in the first embodiment of the invention.

The sheet 131 is preferably 0.3 mm to 5 mm in thickness, more preferably 0.3 mm to 3 mm, and most preferably 0.3 mm to 1.5 mm. If the thickness is less than 0.3 mm, it is difficult to provide barrier cuffs capable of exhibiting the effects of improved fitness, the capacity for absorbing a body fluid is increased, and so forth. In addition, the sheet 131 tends to become twisted when folded. In contrast, if the thickness is more than 5 mm, the rigidity of the absorbent sheet 131 is excessively increased which spoils the fitness. Thus, the desired effect cannot be obtained and the perception of disorder is given to the wearer.

With respect to the fiber or the hydrophilic fiber, it is the same as the first embodiment of the first aspect of the present invention.

With respect to the binder, a hot melting adhesive fiber and strengthening assistant is used when the absorbent sheet 131 is formed similarly as in the first embodiment of the first aspect of the present invention.

As examples of the absorbent sheet 131, there can be included the same sheets as disclosed in the first embodiment of the present invention. Such an absorbent sheet can preferably be used also with a view to obtaining an appropriate degree of shrinkage of the liquid-shrinkable member in accordance with the discharged quantity of body fluid.

In order for the barrier cuffs 140, 140 not to give the perception of disorder to the wearer and in order for the absorbent sheet to exhibit a favorable absorptive capacity of body fluid at the barrier cuffs 140, 140, the barrier cuffs 140, 140 are preferably 3 mm to 30 mm in width W, and more preferably 5 mm to 20 mm. Further, the barrier cuffs are preferably 1 mm to 10 mm in height T, and more preferably 1 mm to 5 mm. If the height T is less than 1 mm, there is the possibility that leakage of body fluid cannot be avoided. In contrast, if the height T is more than 10 mm, the perception of disorder is given to the wearer.

It is good enough that the folding width (widthwise distance from the left and right opposing side edges of the central band-like portion 131a to that point of the side of the back layer 120 of the central band-like portion where the absorbent sheet 131 is folded back) of the absorbent sheet 131 is, in combination with those of the left and right opposing side portions, equal to or more than one half of the width of the central band-like portion 131a.

The liquid-shrinkable members 150 can be selected from film, fiber, threads made of fiber, and foamed bodies, etc. with no particular restriction. Those capable of shrinking by 10% or more, particularly 20% or more, on being impregnated with a body fluid are preferred. Materials for the liquid-shrinkable members 150 include modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and cross-linked fiber thereof; wool or silk modified in the same manner as described above; modified synthetic fiber, such as partially saponified acrylonitrile series of fiber and vinilon fiber which is partially esterified by maleic acid; and threads made of these fibers.

Combined twisted yarn made of a mixture of the above described shrinkable fibers and non-shrinkable fibers or threads are also used preferably in order to provide the liquid-shrinkable member improved strength when it is wet.

In order to bend the barrier cuffs 140, 140 into a configuration nicely complying to the wearer's contacted part, the liquid-shrinkable members 150, 150 are preferably capable of shrinking at at least the generally central portions of the barrier cuffs 140, 140 in the longitudinal direction.

As the liquid-shrinkable members 150, 150 get wet and elastically contract in the longitudinal direction, the barrier cuffs 140, 140 stand up in direction, thereby preventing liquid leakage more securely. The height T of the barrier cuffs 140, 140 becomes higher after the liquid-shrinkable members 150, 150 contract than before they contract, and is preferably 1 to 30 mm, more preferably 3 to 30 mm.

As for the viscous agent for forming the viscous portions 125, 125 and the peelable paper 160, those, which have heretofore been used, can be used without any particular limitation.

In the sanitary napkin 101 of this embodiment, when the barrier cuffs 140, 140 contact the wearer, the body fluid which invades into the barrier cuffs 140, 140 is absorbed primarily by the central band-like portion 131a. Then, the part of the body fluid, which is not absorbed at the central band-like portion 131a, migrates to the side piece portions 131b, 131b. At this time, the liquid-shrinkable members 150, 150 are elastically shrunk by the body fluid. As a consequence, as shown in FIGS. 12 and 13, the absorbent member 130 is bent over the entire length so as to correspond to the wearer's contacted part and thus, the barrier cuffs 140, 140 are further extended on the side of the skin contacting surface. The body fluid migrates to the side piece portions 131b, 131b and further migrates to the layer on the side of the back layer 120 either along the folded forms of the side piece portions 131b, 131b or directly and then absorbed.

According to the sanitary napkin 101 of this embodiment, the barrier cuffs 140, 140 at the left and right side portions fill a gap between the sanitary napkin 101 and the wearer's body and effectively form the leakage-preventive barriers to prevent any leakage of body fluid. Since there is a provision of the barrier cuffs 140, 140 formed by the absorbent member 130, a large quantity of body fluid is absorbed into the absorbent member 130 at the left and right opposing side portions. Therefore, even in the case of a large quantity of body fluid and even in the case of dynamic motion of the wearer, the possible leakage of body fluid can be effectively prevented at the left and right opposing side portions.

According to the sanitary napkin 101 of this embodiment, when a body fluid exceeds a prescribed value in quantity, the barrier cuffs 140, 140 are bent in the longitudinal direction corresponding to the wearer's contacted part, in accordance with the shrinkage of the liquid-shrinkable members 150, 150. The barrier cuffs 140, 140 at the left and right opposing side portions nicely fit the wearer's contacted part, thereby the possible leakage of body fluid can effectively be prevented irrespective of the motion of the wearer.

The napkin 101 can be easily manufactured in a state wherein the liquid-shrinkable members 150, 150 do not have elasticity and the barrier cuffs 140, 140 are not shrunk.

In particular, according to the sanitary napkin 101 of this embodiment, since the barrier cuffs 140, 140 are held in their upstanding postures on the side of the wearer's skin from the left and right opposing sides thereof due to shrinkage of the liquid-shrinkable members 150, 150, the possible leakage of body fluid can be reliably prevented, even in the case where the body fluid is large in quantity and even in the case where the motion of the wearer is active.

In particular, according to the sanitary napkin 101 of this embodiment, since the barrier cuffs 140, 140 are composed of the absorbent sheet 131, the liquid-shrinkable members 150, 150 can easily be arranged on the barrier cuffs by merely securing the liquid-shrinkable members to the absorbent sheet 131 or by disposing the liquid-shrinkable members in the folded portion of the absorbent sheet and securing them to the sanitary napkin 101 at the opposite end portions thereof. When the liquid-shrinkable members, 150, 150 are secured to or disposed on the absorbent sheet 131, the gather-like irregularities formed on the absorbent member 130 by shrinkage of the liquid-shrinkable members 150, 150 are comparatively small and therefore, contact with the wearer's skin is not adversely affected on the side of the top layer 110 so that a comfortable wearing perception can be maintained.

In particular, according to the sanitary napkin 101 of this embodiment, since the multilayer structure is formed at the barrier cuffs 140, 140 by folding a single absorbent sheet 131, the body fluid rapidly migrates through the barrier cuffs 140, 140 along the absorbent sheet 131 and is absorbed. Thus, the possible leakage of the body fluid is effectively prevented.

Figure 14:
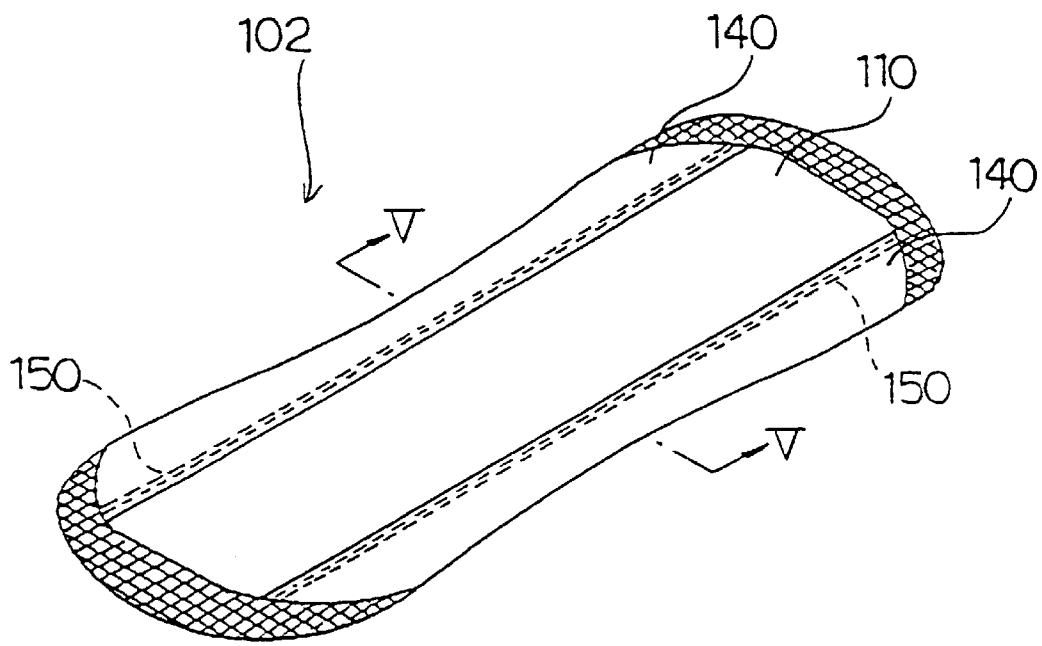
FIG. 14 is a perspective view showing a sanitary napkin as a second embodiment of an absorbent article of the present invention (the second aspect of the invention)
Figure 15:
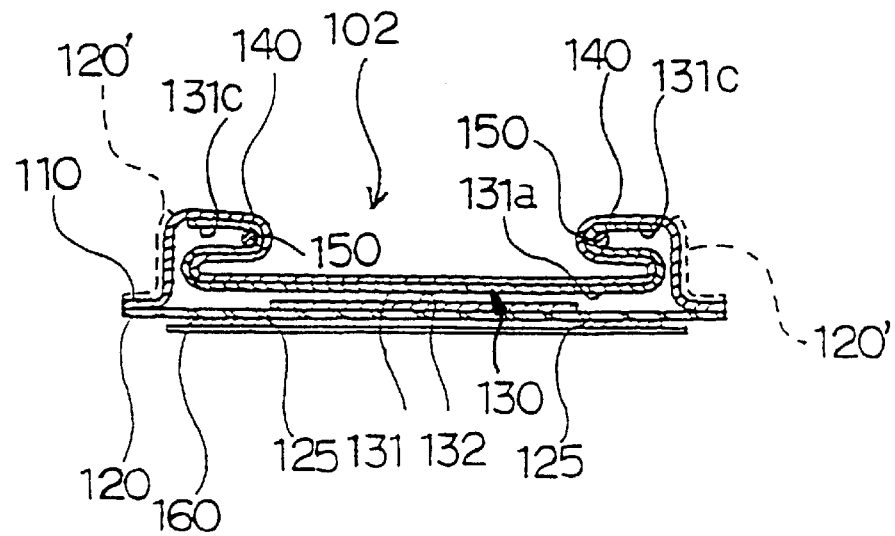
FIG. 15 is a sectional view, taken on line V—V, of FIG. 14, when viewed in the direction as indicated by arrows.
Figure 16:
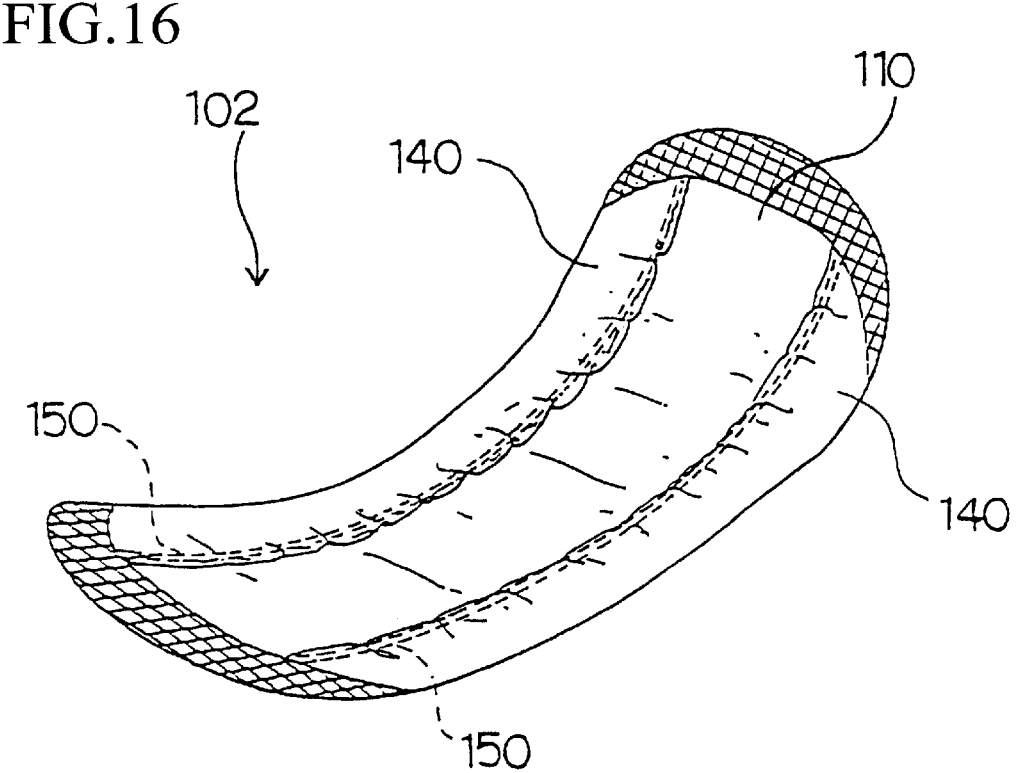
FIG. 16 is a perspective view showing the state of the sanitary napkin of FIG. 14 after absorption of a body fluid.
Figure 17:
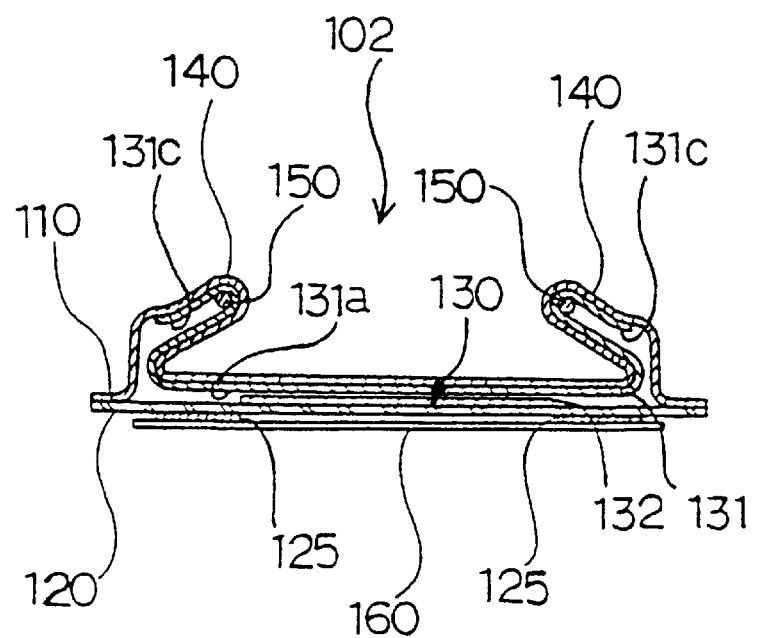
FIG. 17 is a sectional view, taken on line V—V, of the sanitary napkin of FIG. 14 after absorption of a body fluid, when viewed in the direction as indicated by arrows.

FIG. 14 is a perspective view showing a sanitary napkin as the second embodiment of an absorbent article of the present invention (the second aspect of the 15 invention), FIG. 15 is a sectional view taken along line V—V of FIG. 14 when viewed in the direction of the arrows; FIG. 16 is a perspective view showing the state of the sanitary napkin of FIG. 14 after absorption of a body fluid, and FIG. 17 is a perspective view taken along line V—V of FIG. 14 after absorption of the body fluid. In this embodiment, those elements identical with the first embodiment of the second aspect of the invention shown in FIGS. 10 to 13 are denoted by identical reference numerals and therefore the description thereof is omitted.

In the sanitary napkin 102 of this embodiment, as shown in FIGS. 14 and 15, the side piece portions 131c, 131c of the absorbent sheet 131 are folded inwardly to the side of the top layer 110 at the left and right opposing side edges of the central band-like portion 131a, superimposed upon the central belt-like portion 131a, and then folded back, outwardly. The top layer 110 is folded into the same folding configuration as the absorbent sheet 131 and integral therewith.

Between the central band-like portion 131a of the absorbent sheet 131 and the back layer 120, a band-like auxiliary sheet 132 is disposed, so that the absorptive capacity of body fluid is increased in the area near the back layer 120. The auxiliary sheet 132, can be similar to the absorbent sheet 131.

The construction of this embodiment is the same as the first embodiment of the present invention (the second aspect of the invention) except that the folding configurations of the absorbent sheet 131 and top layer 110 are different and there is provided the auxiliary sheet 132.

As shown in FIGS. 16 and 17, the absorbent member 130 is bent in the longitudinal direction complying with the wearer's contacted part and the barrier cuffs 140, 140 are extended in the upward direction due to shrinkage of the liquid-shrinkable members 150, 150, so that the same function and effect as the first embodiment can be obtained.

Moreover, according to the sanitary napkin 102 of this embodiment, since the barrier cuffs 140, 140 functioning as a leakage-preventive barrier, are folded inwardly, the sanitary napkin is transfigured into a shape similar to a vessel or container after absorption of a body fluid, so that the absorptive and retentive capacity of body fluid is more effectively increased.

The present invention (the second aspect of the invention) should not be limited to the above-mentioned first and second embodiments. The specific shape, dimension, etc. of each member can appropriately be modified without departing from the spirit and scope of the present invention (the second aspect of the invention).

Figure 18:
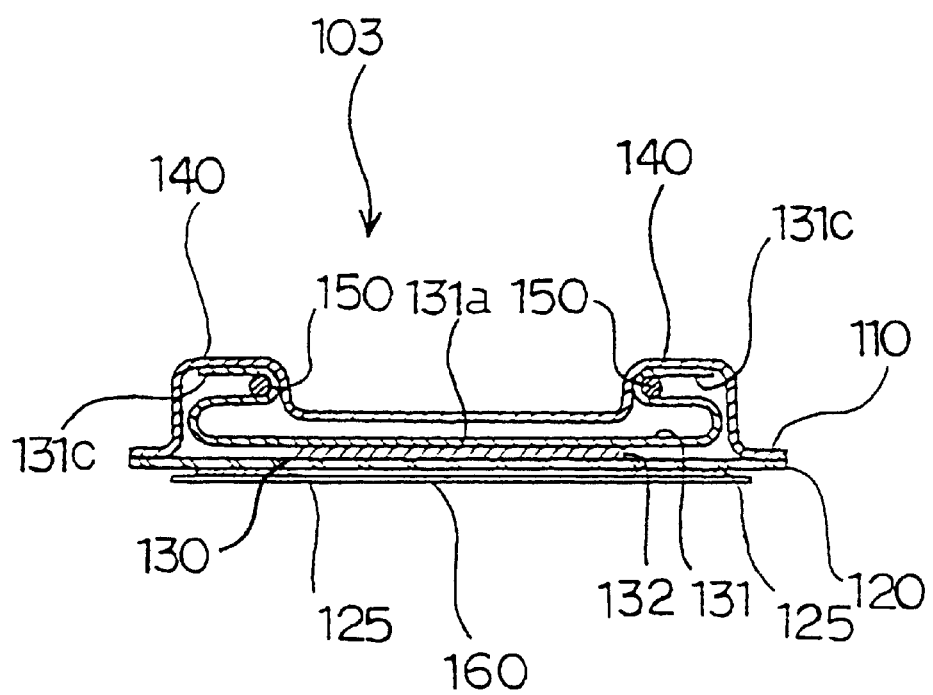
FIG. 18 is a vertical sectional view, corresponding to FIG. 11 of the first embodiment, showing another embodiment of the absorbent article of the present invention (the second aspect of the invention).

For example, it is also acceptable that, in the first and second embodiments, the entire surface of the absorbent sheet 131 is not overlaid on the top layer 110 but only the surface of the absorption sheet 131 which is exposed without being folded is overlaid on the top layer 110. FIG. 18 shows such a sanitary napkin 103, in which, in the second embodiment shown in FIGS. 14 to 17, only a surface of the absorbent sheet 131, which is exposed without being folded, is overlaid on the top layer 110.

In the first and second embodiments, it is also acceptable that the side edge portions of the back layer 120 are extended to form leakage-preventive barriers 120', 120' on the outward side of the absorbent member 10 as indicated by dotted lines of FIGS. 11 and 15. Alternatively, leakage-preventive materials having liquid-impermeable properties can be arranged so that possible leakage of body fluid is more reliably prevented. The leakage-preventive barriers 120', 120' and the leakage-preventive materials may be disposed between the absorbent member 130 and the top layer 110, or they may be arranged outwardly of the top layer 110. In these cases, by firmly attaching the top layer 110 and the leakage-preventive barriers 120', 120' or leakage-preventive materials to the back layer 120 by heat fusion bonding at the perimeter of the absorbent sheet 131, the leakage-preventive barriers 120', 120' or leakage-preventive materials are held in their erected postures so that a more favorable effect can be obtained.

In the first and second embodiments, the absorbent member 130 may be composed of an absorbent pad having a thickness greater than the absorbent sheet 131.

In the first embodiment of FIGS. 10 through 13, the absorbent member may also be provided with an auxiliary sheet as in the second embodiment of FIGS. 14 through 17.

In the first and second embodiments, the side piece portions 131b, 131b, 131c, 131c of the absorbent sheet 131 may also be arranged on the back layer 120 by being folded back again from the vicinity of the side edge of the back layer 120, so that the same effect as the auxiliary sheet 132 can be obtained.

In the first and second embodiments, the side piece portions 131b, 131b, 131c, 131c of the absorbent sheet 131 may be folded and superposed one upon another a greater number of times, so that the barrier cuffs 140, 140 are each folded into multilayer structures.

In the first and second embodiments, the multilayered structure in the barrier cuffs 140, 140 may be formed by a plurality of absorbent sheets.

In the first and second embodiments, the absorbent sheet 131 and the top layer 110 may be formed into a single sheet.

In the first and second embodiments, the absorbent article may be something other than the sanitary napkin, such as an incontinent pad, mother's milk pad, and the like.

In addition, each embodiment described as the first aspect of the invention may be mutually and appropriately compatible with each embodiment described as the second aspect of the invention.

INDUSTRIAL APPLICABILITY

As described hereinbefore, according to the absorbent article of the present invention the possible leakage of body fluid can be effectively prevented irrespective of the quantity of body fluid and the motion of the wearer.

As described hereinbefore, according to the absorbent article of the present invention, the absorbent article is bent in the longitudinal direction complying with the wearer's contacted part, and the possible leakage of body fluid, which is deposited on the top layer without being absorbed by the barrier cuffs at the left and right opposing side portions, is avoided. Moreover, since a large quantity of body fluid is absorbed at the barrier cuffs, the possible leakage of body fluid can be reliably prevented irrespective of the quantity of body fluid and motion of the wearer. In addition, an absorbent article can easily be manufactured in a state wherein the liquid-shrinkable members do not have elasticity and the barrier cuffs do not shrink.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising:
   a liquid-permeable outermost, skin-contactable top layer, a liquid-impermeable back layer, and a liquid-retentive absorbent member;
   said top layer is secured to said liquid-impermeable back layer and said liquid-retentive absorbent member is interposed between said top layer and said back layer;
   said absorbent member includes an absorbent sheet having a thickness of 0.3 mm to 5.0 mm, an entire surface of said absorbent sheet being overlaid with said top layer; and
   only the edge portions of said absorbent member and the portions of said top layer overlying said edge portions are integrally folded inwardly toward a center of said absorbent member and outwardly away from the center of the absorbent member to form an opposing pair of absorbent barrier cuffs having an overlapping, serpentine configuration, and which extend along respective longitudinal edge portions of the absorbent article, said back layer and a remaining portion of said absorbent member being oriented in a un-folded state.

2. The absorbent article according to claim 1, wherein said barrier cuffs are 1 to 10 mm in height, 5–30 mm in width and 5–40% of a smallest width of the absorbent article.

3. The absorbent article according to claim 1, wherein said absorbent sheet comprises a superabsorbent polymer interposed between a pair of sheets of paper or a pair of sheets of nonwoven fabric or between a sheet of paper and a sheet of nonwoven fabric.

4. The absorbent article according to claim 1, wherein said absorbent sheet is obtained by admixing a hydrophilic fiber, a superabsorbent polymer and a binder, and forming the admixture into a sheet-like shape.

5. The absorbent article according to claim 4, wherein the absorbent sheet comprises a hydrophilic fiber, a thermally fusible bonding fiber or a strengthening assistant, and a superabsorbent polymer;

said superabsorbent polymer not being present on an absorbent surface of said absorbent sheet for absorbing liquid but rather distributed inside said absorbent sheet, and being adhered to said hydrophilic fiber constituting said absorbent sheet;

said superabsorbent polymer being spread in an amount of 5 to 300 g/m² of said absorbent sheet; and said absorbent sheet has a thickness of 0.3 to 1.5 mm.

6. The absorbent article according to claim 1, wherein said barrier cuffs have a height of 1 to 30 mm, and elastic members are provided inside side edges of said barrier cuffs located along a longitudinal direction of said barrier cuffs such that said barrier cuffs are shrunk along the longitudinal direction of said barrier cuffs over a prescribed length.

7. The absorbent article according to claim 6 wherein said elastic members are stressed at 10 to 300 gf when at 30% expansion.

8. The absorbent article according to claim 6 wherein said elastic members are disposed over a length of 15 to 90% of a longitudinal length of the absorbent article.

9. The absorbent article according to claim 6, wherein said elastic members are liquid-shrinkable members, which can elastically shrink upon absorption of liquid.

10. The absorbent article according to claim 9, wherein said liquid-shrinkable members are secured to the absorbent sheet or disposed in the folds of the absorbent sheet.

11. A sanitary napkin made of the absorbent article of claim 9.

12. The absorbent article according to claim 1 which is for use as a sanitary napkin.

13. The absorbent article according to claim 1, wherein the top layer extends beyond a perimeter of the absorbent sheet of the barrier cuffs and is secured to the back layer at the perimeter of the absorbent sheet.

14. The absorbent article according to claim 1, wherein the integral fold inwardly toward the center of the absorbent member is toward a top sheet side of said absorbent member.

15. The absorbent article according to claim 1, wherein the integral fold inwardly toward the center of the absorbent member is toward a back layer side of said absorbent member.

16. An absorbent article comprising a liquid-permeable outermost, skin-contactable top layer, a liquid-impermeable back layer and a liquid-retentive absorbent member;

said top layer is secured to said liquid-impermeable back layer and said liquid-retentive absorbent member is interposed between said top layer and said back layer;

an entire surface of said absorbent member is overlaid with said top layer; and only the edge portions of said absorbent member and the portions of said top layer overlying said edge portions are integrally folded inwardly toward a center of said absorbent member and outwardly away from the center of the absorbent member to form an opposing pair of absorbent barrier cuffs having an overlapping, serpentine configuration, and which extend along respective longitudinal edge portions of the absorbent article, said back layer and a remaining portion of said absorbent member being oriented in an un-folded state.

17. The absorbent article according to claim 16 wherein the absorbent member is an absorbent sheet.

18. The absorbent article according to claim 16, wherein only the top layer of each of the barrier cuffs is secured to the back layer.

19. The absorbent article according to claim 16, wherein the integral fold inwardly toward the center of the absorbent member is toward a top sheet side of said absorbent member.

20. The absorbent article according to claim 16 wherein the integral fold inwardly toward the center of the absorbent member is toward a back layer side of said absorbent member.

* * * * *